(12) United States Patent
De Zeeuw et al.

(10) Patent No.: US 6,301,952 B1
(45) Date of Patent: Oct. 16, 2001

(54) GAS CHROMATOGRAPHIC DEVICE

(75) Inventors: Jaap De Zeeuw; Jan Adriaan Peene; Rene Cornelis Maria de Nijs, all of Middleburg (NL)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 09/471,661

(22) Filed: Dec. 24, 1999

(30) Foreign Application Priority Data

Dec. 30, 1998 (EP) .................................................. 98204484

(51) Int. Cl.⁷ ........................... G01N 31/08; G01N 30/02; B01D 15/08
(52) U.S. Cl. ........................ 73/23.35; 73/23.42; 73/23.39; 73/864.87; 210/656
(58) Field of Search ................................ 73/23.35, 23.37, 73/23.41, 23.39, 23.42, 61.55, 61.56, 864.21, 864.72, 864.87; 210/656, 659

(56) References Cited

U.S. PATENT DOCUMENTS

| | | | |
|---|---|---|---|
| 2,920,478 | * | 1/1960 | Golay ........................................ 73/23 |
| 3,049,909 | * | 8/1962 | Thomas .................................... 73/23 |
| 3,077,766 | * | 2/1963 | Reinecke .................................. 73/23 |
| 3,119,252 | * | 1/1964 | Nerheim ................................... 73/23 |
| 3,400,514 | * | 9/1968 | Noda ...................................... 55/158 |
| 3,421,292 | * | 1/1969 | Llewellyn .............................. 55/158 |
| 3,455,092 | * | 7/1969 | Llewellyn .............................. 55/158 |
| 3,471,692 | * | 10/1969 | Llewellyn et al. ................... 250/41.9 |
| 3,483,731 | * | 12/1969 | Sanford et al. ........................ 73/23.1 |
| 3,537,297 | * | 11/1970 | Loyd et al. ............................ 73/23.1 |
| 3,589,171 | * | 6/1971 | Haley et al. ........................... 73/23.1 |
| 3,772,909 | * | 11/1973 | Anderson ............................... 73/23.1 |
| 3,798,973 | * | 3/1974 | Estey ................................. 73/422 GC |
| 3,926,561 | * | 12/1975 | Lucero ................................. 23/232 R |
| 4,215,563 | * | 8/1980 | Clardy et al. ......................... 73/23.1 |
| 4,479,380 | * | 10/1984 | Novotny et al. ................... 73/61.1 C |
| 5,236,668 | * | 8/1993 | Higdon ................................... 422/89 |
| 5,340,543 | * | 8/1994 | Annino et al. .......................... 422/89 |
| 5,719,322 | * | 2/1998 | Lansbarkis et al. ................. 73/23.39 |

\* cited by examiner

*Primary Examiner*—Daniel S. Larkin
*Assistant Examiner*—David J. Wiggins
(74) *Attorney, Agent, or Firm*—Bella Fishman; Edward H. Berkowitz

(57) ABSTRACT

A gas chromatographic device has an inlet system, a column and a pressure reducing means combined and assembled in such a series arrangement that provides adequate system performance with shorter wide bore column length and shorter sample analysis times needed during a peak integration and evaluation process performed by a connected mass spectrometer system. Pressure reducing means may be integral part of the inlet system or the column when positioned between the inlet system and the column. Pressure reducing means preferably positioned before the column and being capable of reducing the pressure prevailing at the inlet of said pressure reducing means to a column outlet pressure which is essentially vacuum. Preferably, the inlet pressure of the device is in a range between 10 kPa and 1000 kPa and the absolute pressure prevailing at the outlet of said pressure reducing means is in a range between 0.00001 kPa and 50 kPa.

24 Claims, 2 Drawing Sheets

GAS CHROMATOGRAPHIC DEVICE

FIELD OF THE INVENTION

The present invention relates to a gas chromatographic device comprising an inlet system, a column and a pressure reducing means. More particularly, the present invention relates to a column for a gas chromatographic device with a pressure reducing means, being capable of operating under vacuum conditions.

BACKGROUND OF THE INVENTION

The market for routine analysis of complex samples requires columns which have a long life time, reduced column bleeding, and sufficient capacity. These columns must also allow for the analysis in a short period of time. In particular, the demand for systems comprising a gas chromatographic device coupled to a mass spectrometer (GC/MS) which are used for various analyses is continuously growing, because these systems get more user friendly, their dimensions get smaller and their purchasing costs keep decreasing. For GC/MS systems the separation capacity of the column is no longer that important. Although for sample analysis some separation capacity is required, in general it is not necessary to utilize long columns. However, in the GC/MS system the inlet pressure of the column is above atmospheric and the outlet pressure of the column is essentially vacuum because the column ends in the ionization chamber of the mass spectrometer. That is why the columns in GC/MS systems are often very long to provide the necessary pressure drop between the inlet and the outlet of the column. Consequently, long periods of time are often required to perform the sample analyses. Smaller bore columns having a reduced length could be used to provide the pressure drop, but these columns have a disadvantage such as a limited sample capability as well as practical problems with regard to installation, operation and elute peaks which are too fast to quantify using mass spectrometry systems.

SUMMARY OF THE INVENTION

The present invention intends to provide a solution for the problems described above. A gas chromatographic device comprises at least an inlet system, a column and a pressure reducing means. The pressure reducing means according to one embodiment of the present invention is disposed between the inlet system and the column. In this embodiment the column outlet is operated under vacuum conditions.

The pressure reducing means according to another embodiment is connected to the outlet of the column. In this embodiment the column outlet pressure is approximately equal to the pressure of the inlet system and the pressure reducing means outlet is operated under vacuum conditions.

In both embodiments the pressure reducing means can be an integral part of the column.

The columns to be used in the gas chromatographic device according to the present invention are relatively reduced in length which enables short analysis times of the samples. The eluting peaks have sufficient peak width (in seconds) to be properly integrated by contemporary mass spectrometry systems. Moreover, the proposed embodiments offer the further benefit that under vacuum the optimal linear gas velocity increases about tenfold and that components elute from the column at lower temperatures, especially important for thermolabile and high boiling components. Additionally, the life time of the column is generally longer than that of conventional columns due to reduced column bleeding. It is also not necessary to couple the column via a restriction to the ionization chamber of the mass spectrometer so that no leaks occur. An additional advantage is that a fixed or standard inlet pressure can be used which is preferably 10 kPa to 1000 kPa, and more preferably 10 kPa to 250 kPa.

According to the present invention the pressure reducing means is such that the pressure prevailing at the outlet of said pressure reducing means is 0.00001 kPa to 50 kPa (absolute pressure), preferably 0.01 kPa to 20 kPa (absolute pressure).

BRIEF DESCRIPTION OF DRAWINGS

The above mentioned features and advantages of the present invention will be described by way of example with references to the accompanying drawings in which:

FIGS. 1a and 1b illustrate two possible positions for the pressure reducing means (1): before or after the column (2) respectively. The column is a short wide-bore open tubular capillary column.

FIG. 2($a$) shows that the C80-fraction elutes of the column at shorter retention times when compared with FIG. 2($b$) without a decreased resolution. Consequently, according to the preferred embodiment of the invention, the pressure reducing means is preferably positioned in front of the inlet of a column.

DETAILED DESCRIPTION OF THE INVENTION

Figure 1A:
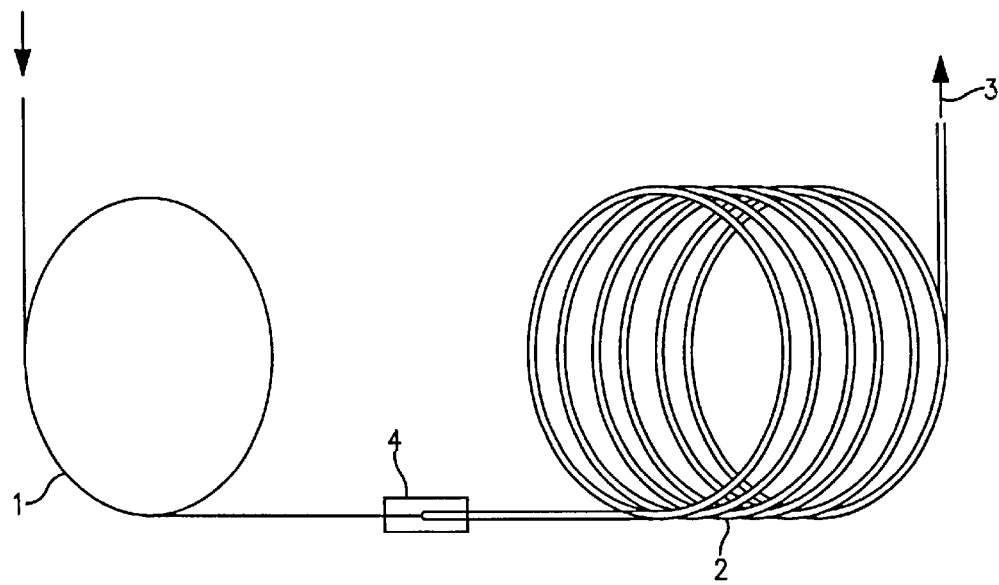
FIGS. 1a and 1b show pressure reducing means (1), column (2) and a coupling device (4) for connecting and integrating the pressure reducing means with the column, arrow (3) indicates the connection to a MS-detector.
Figure 1B:
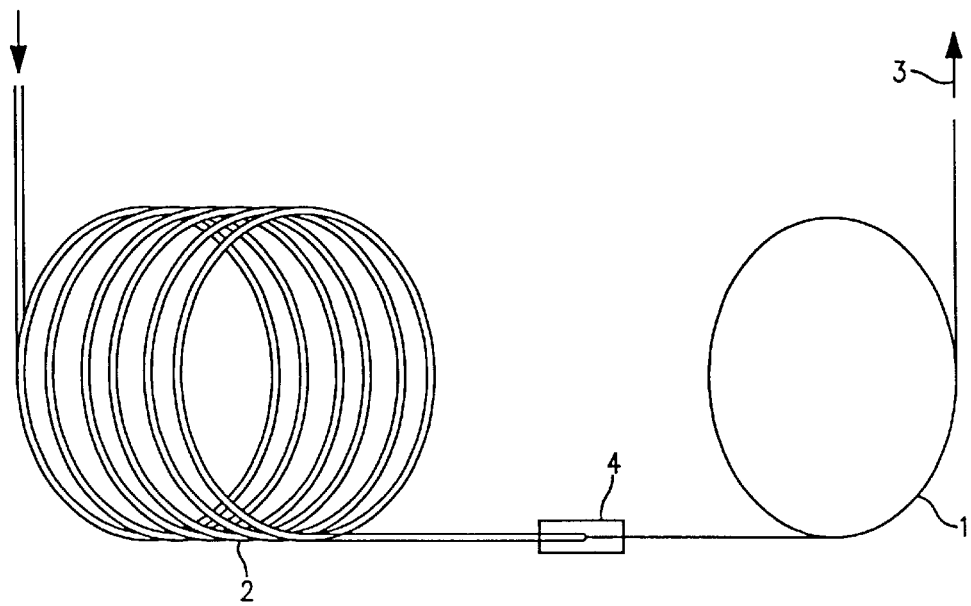
Figure 2A:
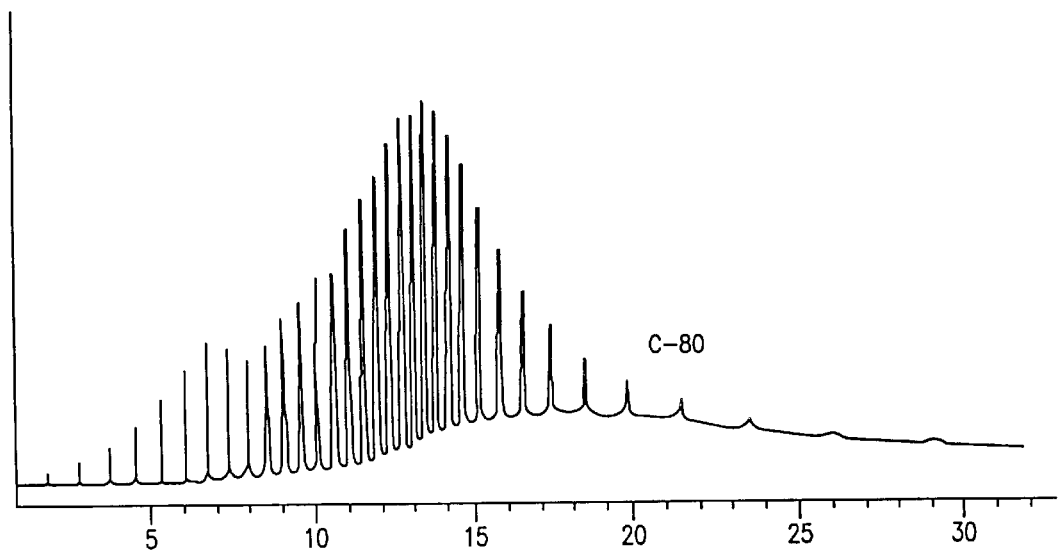
FIGS. 2a and 2b show two GC/MS-chromatograms of Polywax 655 obtained with the embodiments shown in FIGS. 1a and 1b respectively (conditions: column: 10 m×0.53 mm; stationary phase: CP-SIMDIST, film thickness: 0.17 micrometer; injection temperature: 350° C.; interface temperature: 350° C.; inlet pressure: 150 kPa; temperature profile: 150° C. (1 min.), 20° C./min. to 400° C.).
Figure 2B:
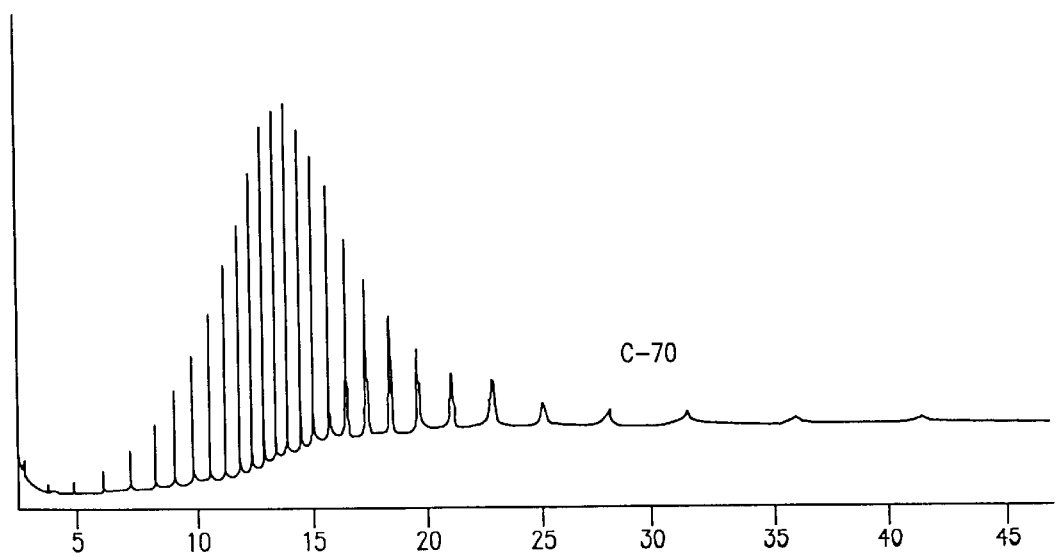

The pressure reducing means according to one embodiment of the present invention is an integral part of the inlet system. Alternatively, it may be positioned between the inlet system and the column. According to yet another embodiment the pressure reducing means is an integral part of the column. Integration with the column is to be realized by coupling the pressure reducing means to the column using coupling devices made of silica, quartz, glass, metal, polyimide or other organic or inorganic polymer or a combination thereof. Alternatively, connectors can be used containing graphite, vespel, graphitized vespel type ferrules. The pressure reducing means is preferably an integral part of the column so that such a column can easily be installed in systems already in use.

According to yet another embodiment of the present invention the pressure reducing means can also be positioned inside the inlet of the column as a frit, packing or by reducing the diameter of the column.

The pressure reducing means has preferably a coiled tubular shape and is preferably made of silica, glass, metal, an organic polymer, and inorganic polymer or a combination thereof. More preferably, the pressure reducing means is made of silica or an organic or inorganic polymer. The column may be made of the same materials as the pressure reducing means. The column has length in a range between 0.25 m to 100 m., preferably 0.5 m to 25 m An average internal diameter of the tube is in a range between 0.05 mm and 1.0 mm, preferably 0.25 mm to 0.75 mm and an average outer diameter in a range between 0.2 mm to 1.0 mm, preferably 0.4 mm to 0.8 mm.

The pressure reducing means that is preferably an integral part of the column has the following dimensions: average internal diameter of 0.001 mm to 0.2 mm, preferably of 0.01 mm to 0.1 mm; average outer diameter of 0.2 mm to 0.8 mm, preferably of 0.3 mm to 0.6 mm; length of 1 mm to 2500 mm, preferably 10 mm to 1000 mm.

According to yet another embodiment of the invention the pressure reducing means which is preferably an integral part of the column is comprised by an opening or hole having a cross section of 0.0001 mm to 0.1 mm, preferably 0.0005 mm to 0.01 mm, and a length of 0.25 mm to 100 mm, preferably 0.5 mm to 10 mm.

The pressure reducing means may also be formed by a capillary tube having an average internal diameter of 0.1 mm 5.0 mm, preferably 0.2 mm to 2 mm, a length of 5 mm to 500 mm, preferably 20 mm to 100 mm, wherein the capillary tube is preferably packed with deactivated or non-deactivated particles having an average size of 0.5 µm to 500 µm (micrometer), preferably 5 µm to 500 µm.

The pressure reducing means may be manufactured by employing micromachining technology using silicon etching/wafer technology. The pressure reducing means may be coated with chemically bonded or cross-linked liquidator solid stationary phases with an average film thickness of 0.001 µm to 50 µm, preferably 0.01 µm to 0.1 µm.

The present invention further relates to a column for a gas chromatographic device comprising a pressure reducing means, said pressure reducing means being capable of reducing the pressure prevailing at the inlet of the column to a column outlet pressure which is essentially vacuum Ind the pressure reducing means being an integral part of the column.

The column has preferably a length of 0.25 m to 100 m, more preferably 0.5 m to 25 m, an average internal diameter of 0.05 mm to 1.0 mm, preferably 0.25 mm to 0.75 mm and an average outer diameter of 0.2 mm to 1.0 mm, preferably 0.4 mm to 0.8 mm.

The column and/or the pressure reducing means are preferably made of silica, glass, metal, an organic polymer, an inorganic polymer or a combination thereof.

The columns utilized by the gas chromatographic devices comprises an inlet system and a pressure reducing means which may have an internal surface which is deactivated with a chemical and/or physical deactivation agent. Examples of suitable deactivation agents are octamethyl tetrasiloxane, hyrosilane or of the polyethylene glycol type. The internal surface of these columns may additionally be coated, not only with bonded and/or cross linked liquid or solid stationary phases, but also with non-bonded and/or non-crosslinked stationary phases having an average film thickness of 0.05 µm to 10 µm. If the columns are coated with a solid stationary phase, the average film thickness thereof is 1 µm to 100 µm, preferably 2 µm to 50 µm.

The columns with the pressure restriction means may be coated on the outside thereof with a single layer or with multiple layers of a organic polymer, e.g. polyimide, metal, salt or another polymeric or ceramic material.

The present invention further relates to columns with the pressure restriction means or the columns as a part of the gas chromatographic devices comprising an inlet system and a pressure reducing means which are wound on a cage or which are mounted on a flat disc. These columns may further comprise a silicone chip.

What is claimed is:

1. A gas chromatographic device comprising: an inlet system, a column and a pressure reducing means disposed therebetween for reducing pressure between an inlet of said pressure reducing means and an outlet of said column, said outlet of said column being under vacuum wherein said column is a wide bore column, wherein said pressure reducing means is formed by a capillary tube having and internal diameter in a range between 0.1 mm to 5.0 mm.

2. The gas chromatographic device of claim 1, wherein the pressure prevailing at said inlet of said pressure reducing means is in a range between 10 kPa, and 1000 kPa and pressure prevailing at said outlet of said column is substantially below an atmospheric pressure.

3. The gas chromatographic device of claim 1, wherein the pressure prevailing at an outlet of said pressure reducing means is in a range between 0.00001 kPa to 50 kPa.

4. The gas chromatographic device of claim 2, wherein said pressure reducing means is an integral part of said inlet system.

5. The gas chromatographic device of claim 2, wherein said pressure reducing means is an integral part of said column.

6. The gas chromatographic device of claim 2, wherein said pressure reducing means is made of a material selected from the group consisting of silica, glass, metal, an organic polymer, and an inorganic polymer.

7. The gas chromatographic device of claim 2, wherein said pressure reducing means is made of a combination of materials selected from the group consisting of silica, glass, metal, an organic polymer, and an inorganic polymer.

8. The gas chromatographic device of claim 2, wherein said pressure reducing means has a coiled tubular shape.

9. The gas chromatographic device of claim 2, wherein said pressure reducing means is formed by a capillary tube having a length in a range between 1 mm and 2500 mm.

10. The gas chromatographic device of claim 9, wherein said capillary tube is packed with particles, having an average size in a range between 0.5 µm and 500 µm.

11. The gas chromatographic device of claim 10, wherein said capillary tube is packed with deactivated particles.

12. The gas chromatographic device of claim 10, wherein said capillary tube is packed with non-deactivated particles.

13. A gas chromatographic device comprising:
an inlet system, a wide bore column having an inlet and an outlet, and a pressure reducing means, said pressure reducing means being coupled to said outlet of said wide bore column for providing a vacuum condition at an outlet of said pressure reducing means, wherein said pressure reducing means is an integral part of said wide bore column.

14. The gas chromatographic device of claim 13, wherein said outlet pressure of said column is substantially equal to an inlet pressure of said inlet system, and said outlet pressure of said pressure reducing means is substantially below an atmospheric pressure.

15. The gas chromatographic device of claim 14, wherein said pressure reducing means is a bore fused silica capillary tube having a length in a range between 5 mm and 500 mm, and an internal diameter in a range between 0.1 mm and 5.0 mm, said capillary tube is packed with particles having an average size in a range between 0.5 µm to 500 µm.

16. The gas chromatographic device of claim 15, wherein said bore fused silica capillary tube has a length in a range between 20 mm and 100 mm, and an internal diameter in a range between 0.2 mm and 2.0 mm, said capillary tube is packed with particles having an average size in a range between 5 µm to 50 µm.

17. The gas chromatographic device of claim 16, wherein said capillary tube is packed with deactivated particles.

18. The gas chromatographic device of claim 16, wherein said capillary tube is packed with non-deactivated particles.

19. The gas chromatographic device of claim 15, wherein said pressure reducing means has an internal diameter in a range between 0.001 mm and 0.2 mm, and a length in a range between 1 mm and 2500 mm.

20. A chromatography column for a gas chromatographic device comprising:

an inlet and an outlet; and a pressure reducing means being an integral part of the column for reducing the pressure prevailing at said inlet to a pressure that is substantially below an atmospheric pressure, wherein said column is a wide bore column that has a length in a range between 0.25 m and 100 m, and has an internal diameter in a range between 0.05 mm and 1.0 mm.

21. The chromatography column of claim 20, wherein said pressure reducing means further comprising an inlet and an outlet, and said pressure reducing means is made of a material or combination of materials selected from the group consisting of silica, glass, metal, an organic polymer, and an inorganic polymer.

22. The chromatography column of claim 21, wherein said column and said pressure reducing means are made of essentially the same material.

23. The chromatography column of claim 21, wherein said outlet of said chromatography column is connected to said inlet of said pressure reducing means forming an integral part therewith.

24. The chromatography column of claim 21, wherein said inlet of said chromatography column is connected to said outlet of said pressure reducing means forming an integral part therewith.

* * * * *